United States Patent [19]

Foster et al.

[11] 4,083,887

[45] Apr. 11, 1978

[54] CARBONYL REMOVAL FROM GASEOUS STREAMS USING ZNS

[75] Inventors: Alan W. Foster; Alfio J. Besozzi, both of Houston, Tex.

[73] Assignee: Petro-Tex Chemical Corporation, Houston, Tex.

[21] Appl. No.: 714,743

[22] Filed: Aug. 16, 1976

Related U.S. Application Data

[60] Division of Ser. No. 420,043, Nov. 29, 1973, Pat. No. 3,998,902, which is a continuation-in-part of Ser. No. 223,363, Feb. 3, 1972, abandoned.

[51] Int. Cl.$^2$ .................... C07C 11/12; C07C 15/00; C07C 11/00; C07C 7/00
[52] U.S. Cl. .......................... 260/680 E; 260/677 A; 260/681.5 R

[58] Field of Search ........ 260/680 E, 677 A, 681.5 R; 423/245, 561 B; 252/439

[56] References Cited

U.S. PATENT DOCUMENTS

| | | | |
|---|---|---|---|
| 1,942,530 | 1/1934 | Bader et al. | 252/439 |
| 3,725,493 | 4/1973 | Stine | 260/680 E |
| 3,850,846 | 11/1974 | Kravitz | 252/439 |

Primary Examiner—O. R. Vertiz
Assistant Examiner—Brian E. Hearn
Attorney, Agent, or Firm—Kenneth H. Johnson

[57] ABSTRACT

Gaseous streams containing carbonyl compounds have the carbonyl content reduced by contacting the gaseous streams with a catalyst of ZnS. Reactor effluent from an oxidative dehydrogenation reaction to produce butadiene-1,3, is contacted with ZnS to remove carbonyl compounds.

1 Claim, No Drawings

CARBONYL REMOVAL FROM GASEOUS STREAMS USING ZNS

This is a division of application Ser. No. 420,043, filed Nov. 29, 1973, now U.S. Pat. No. 3,998,902, which was a continuation-in-part of Ser. No. 223,363, filed February 3, 1972, now abandoned.

This application relates to a process for the reduction in carbonyl impurities in gaseous streams. A preferred embodiment relates to a process for the purification of unsaturated hydrocarbons from a gaseous mixture containing hydrocarbons, relatively non-condensable gases and carbonyl compounds as an impurity.

Unsaturated hydrocarbons are commercially produced by the catalytic dehydrogenation of more saturated hydrocarbons. For example, diolefins are produced in large quantities by the dehydrogenation of saturated hydrocarbons or olefins.

Improved processes for the preparation of unsaturated hydrocarbons such as butene butadiene-1,3 isoprene and styrene are processes whereby hydrocarbons such as butane, butene, isopentenes or ethyl benzene are dehydrogenated at elevated temperatures in the presence of catalysts and oxygen and such processes are known as oxidative dehydrogenation processes. Superior results and yields of product are thereby obtained. However, the product streams contain not only the desired unsaturated hydrocarbon, but also various oxygenated compounds such as aldehydes and other carbonyl compounds. When air is used as the source of the oxygen, the effluent from the dehydrogenation reactor will contain large quantities of relatively non-condensable gases, such as nitrogen. The gaseous effluent may also contain varying amounts of steam. It is one of the principal objects of this invention to provide a process for the separation of the carbonyl and other oxygenated compounds from the gaseous stream containing hydrocarbons.

The oxygenated compounds are a serious contaminant in the unsaturated hydrocarbon product and must be essentially completely removed in order to have a product of suitable purity, e.g., a product having on the order of a few parts per million carbonyl compounds. The essentially complete removal of the oxygenated compound is quite difficult for several reasons. In the first place, the oxygenated compounds constitute only a very minor percentage of the gaseous stream to be purified. Normally the carbonyl compounds will constitute less than 5 mol percent of the gaseous stream to be purified and more usually may constitute such as less than or up to 2.5 mol percent of the gaseous stream. Generally the feed stream will contain at least about 10 ppm carbonyl compounds based on the other organic compounds such as the hydrocarbons. The oxygenated compounds are therefore quite difficult to remove because of their low concentrations in the gaseous stream. In addition, the oxygenated compounds may be difficult to separate from compounds such as hydrocarbons regardless of their relative concentration. Azeotropes may form between the oxygenated compounds and various hydrocarbons. For instance, an azeotrope is formed between acetaldehyde and butadiene-1,3. It is therefore an object of this invention to promote a process for the removal of carbonyl compounds from a gaseous stream containing only minute quantities of carbonyl compounds based on the total gaseous stream.

Prior processes have dealt with the separation of oxygenated compounds from oxidative dehydrogenation processes. In U.S. Pat. Nos. 3,308,201 and 3,336,414 oxygenated compounds are removed by scrubbing with an aqueous composition. These processes have the drawback that the carbonyl compounds are transferred to a scrubbing water and must still be disposed of such as by biodegradation. According to U.S. Pat. No. 3,557,238 the carbonyl compounds are condensed with the steam from the reactor effluent, revaporized and fed back to the dehydrogenation reactor. Therefore, one object of this invention is to provide a process for the destruction of carbonyl compounds. It is a further object to destroy the carbonyl compounds without significantly losing reactor product or significantly isomerizing any of the products. It is also an object to produce a catalyst which has long catalyst life and which has a reduced tendency to form coke. Another object is to provide a process which is paticularly effective in destroying formaldehyde because formaldehyde is difficult to economically separate from aqueous compositions.

According to this invention is has been discovered that the elements and compounds thereof of Periodic Table* Groups 1a. 1b. 2a. 2b. 3b. 4b. 6b. 7b. 8 and mixtures catalyze the destruction of oxygenated compounds in vapor phase. Thus, it is possible to contact the reactor effluent directly with a catalyst bed and destroy oxygenated compounds.

*All references in this application are to the Periodic Table as found on page B-3 of the 51st. edition of the Handbook of Chemistry & Physics (1970–71 Chemical Rubber Publishing Company).

A particular and preferred group of these materials have been found to provide reduced carbonyl content of a contacted gaseous stream when employed alone. The elements, particularly the metals or metalloids of Periodic Table Groups 2a, 2b, 4b, 8 and Ce have demonstrated the capacity to substantially reduce the carbonyl content of a gaseous stream when employed alone as the principal or major cation component of the catalyst.

The atoms may be present such as in the form of the metal compounds such as oxides, salts or hydroxides. Many of these metals, salts and hydroxides may change during the preparation of the catalyst, during heating in a reactor prior to use in the process of this invention, or are converted to another form under the described reaction conditions, but such materials still function as an effective catalyst in the defined process to give carbonyl removal or destruction. For example, the metal may be present as the nitrates, nitriles, carbonates, hydroxides, acetates, sulfites, silicates, sulfides and the like. For instance, iron nitrate and iron sulfate may be converted at least to some extent to the corresponding oxides while being heated in a reactor to a reaction temperature of about 550° C. Such salts of the defined metal groups, which are normally stable at the defined reaction temperatures may likewise be effective under the conditions of the described reaction. However, some metal compounds are more effective than other compounds of the same metal and, therefore, the compound giving the most effective results can be chosen. Preferably, catalysts solid under the conditions of carbonyl removal will be used. Preferably, the compound will exhibit some basicity e.g. as in the case of oxides, carbonates or hydroxides. It has been found that prior art compositions that are known as thermal or oxidative dehydrogenation catalysts or as hydrogenation catalysts have been effective to destroy carbonyl compounds according to this invention.

Examples of preferred catalysts are Zr, Zn, Ca, Co, Sr, Fe, Ti, Pd or Ce. In the Periodic Table Group 8 elements Fe and the Platinum group metals are preferred with Fe being particularly preferred. Useful compounds include, for example, berylium oxide, magnesium acetate, magnesium bromide, magnesium oxide, magnesium iodide, calcium oxide, calcium acetate, calcium oxalate, calcium chloride, calcium bromide, calcium iodide, calcium fluoride, calcium carbonate, strontium nitrate, strontium chloride, strontium oxide, strontium hydroxide, strontium carbonate, strontium bromide, barium oxide, barium chloride, barium hydroxide, barium sulfate, barium bromide, barium iodide, beryllium chloride, zinc fluoride, zinc oxide, zinc ortho phosphate, zinc phosphide, zinc orthosilicate, zinc metasilicate, zinc sulfide, cadmium oxide, titanium dioxide, zirconium oxide, $CrBr_2$, $Cr_2O_3$, ferrous oxide, ferric oxide, $Fe_3O_4$. The platinum metal elements are the elements in the Fifth and Sixth Periods of Group 8 of the Periodic Table. These elements are ruthenium, rhodium, palladium, osmium, iridium, platinum. Preferred catalysts are platinum, palladium, compounds thereof, and mixtures of these. Suitable catalysts are such as palladium metal, palladium monoxide, platinum oxide(ous), platinum metal, platinum-rhodium alloys and the like. The elements of Groups 2a, 2b, 4b, 8 and Ce are the main active constituents of the catalyst. Aluminum can be present in fairly large amounts but the exact function of aluminum is not known as aluminum by itself does not particularly catalyze the reaction. Oxides, hydroxides, or carbonates or compounds which are converted to these compounds under the conditions of reaction to destroy the carbonyl compounds are preferred. Ingredients or anions which suppress or deactivate the effect of the defined metal elements should be avoided.

Excellent catalysts are those which contain calcium as an ingredient such as CaO or more preferably calcium combined with aluminum and/or silicon such as calcium aluminate or calcium silicate. The use of cement is claimed in an application by Harold F. Christmann, Ser. No. 223,364, filed Feb. 3, 1972, now U.S. Pat. No. 3,801,669 and entitled PURIFICATION OF HYDROCARBONS. Cements are combinations of calcium, aluminum and silica as main ingredients and may be prepared e.g. by the sintering of a mixture of calcium carbonate (as limestone) with an aluminum silicate. Cements are discussed on pages 684–696 volume 4 of Kirk-Othmer, Encyclopedia of Chemical Technology, 2nd. edition (1964) which disclosure is hereby incorporated by reference. Portland cements are classified by Types I, II, III, IV and V (ASTM C 150 – 63) and a preferred type according to the copending application is Type III. Typical cements would have by weight from about 15 or 20 percent silicon analyzed as $SiO_2$, from about 2 to 6 or 8 percent aluminum analyzed as $Al_2O_3$ (or up to about 45 percent for the high alumina cements, and from about 55 or 60 to 66 or 70 weight percent calcium analyzed as CaO, or down to about 30 percent CaO for the high alumina cements). The cements may also contain minor ingredients such as MgO and $SO_3$. The specification for Type III Portland is that it have by weight a mixture of 5 percent MgO; when the $3CaO \cdot Al_2O_3$ is 8 percent or less the $SO_3$ should be at a maximum of 3.0 percent and when the $3CaO \cdot Al_2O_3$ is more than 8 percent the $SO_3$ should be 4.0 percent maximum; the loss on ignition is 3 percent maximum and the insoluble residue is 0.75 percent maximum.

The catalysts of this invention may be used as such or may be coated in catalyst carriers. Catalyst carriers are known in the art and include such compounds as alumina, silica, silicon carbide and so forth. Diluents may also be incorporated into the catalyst so long as the diluent does not prevent the catalyst from functioning. Preferably the carrier should be low surface and low acidity.

The gaseous mixture to be treated containing the carbonyl* compounds as an impurity may be obtained from a variety of sources. However, the invention is particularly suitable for the purification of gaseous effluents resulting from the oxidative dehydrogenation of organic compounds including hydrocarbons utilizing air or oxygen diluted with non-condensable diluents such as nitrogen or helium. Examples of oxidative dehydrogenation processes are disclosed, e.g. in U.S. Pat. Nos. 3,207,805; 3,284,536; 3,320,329; 3,342,890; and 3,476,824.

*All references to overall quantities of carbonyl compounds are determined by ASTM Method D-1089 and reported as acetaldehyde. The procedure is modified to exclude the analysis of acetals. Generally, the carbonyl compounds will have from 1 to 8 carbon atoms, e.g. from 1 to 6 carbon atoms when a $C_4$ to $C_6$ compound is being dehydrogenated, and will have from 1 to 2 carbonyl groups. Formaldehyde is included in this definition.

Organic compounds to be dehydrogenated may be acyclic, cycloaliphatic or alkyl aryl compounds of 3 or 4 to 9 carbon atoms, which contain at least two adjacent carbon atoms, each of which carbon atom has at least one hydrogen atom attached. Olefins, diolefins or compounds may be produced from more saturated compounds e.g. butadiene-1,3 may be produced from n-butane. A mixture of monoolefins and diolefins may also be produced such as a mixture of butadiene-1,3 and butenes from a feedstock of a mixture of n-butane and butene. Cyclohexane may be dehydrogenated to cyclohexene and/or benzene. Ethyl benzene or ethyl cyclohexane may be dehydrogenated to styrene. Good results may be obtained with an organic feed containing at least 50, such as at least 75 mol percent of an acyclic aliphatic hydrocarbon. Hydrocarbons of 4 to 5 carbon atoms having a straight chain of at least four carbon atoms, e.g., those having a single double bond have been used and preferred are the monoethylenically unsaturated compounds or mixtures of saturated and monoethylenically unsaturated compounds. Hydrocarbons having from 4 to 8 carbon atoms constitute a preferred feed with n-butane, n-butene, isopentane, isopentene, ethyl benzene and mixtures having given excellent results.

Oxygen will generally be supplied to the dehydrogenation zone in the range of about 0.20 mol of oxygen to 2.0 or 3.0 mols of oxygen per mol of hydrocarbon to be dehydrogenated. A preferred range for the oxygen is from about 0.3 to 1.50 mols of oxygen per mol of hydrocarbon to be dehydrogenated. Either air, oxygen or oxygen diluted with a diluent such as nitrogen, helium, and the like, may be utilized. The oxygen may be supplied in gaseous form or via a solid oxygen carrier such as in U.S. Pat. No. 3,420,911. Steam may be fed to the dehydrogenation zone in amounts such as from about 2 to 40 mols of steam per mol of hydrocarbon to be dehydrogenated. An advantageous range is from 2 to 20 mols of steam per mol of hydrocarbon.

The dehydrogenation reaction may be conducted in the absence of contact catalysts, but better results are obtained if the reaction is conducted in the presence of metal or metal compound catalysts. The dehydrogenation reactor may be a fixed or fluid bed reactor. Reactors conventionally used for the dehydrogenation of hydrocarbons to butadiene may be employed. The total pressure in the dehydrogenation zone may suitably be about atmospheric pressure. However, higher pressures or vacuum may be used. Pressures such as from about atmospheric (or below) up to about 100 to 200 p.s.i.g. may be employed. The dehydrogenation reaction will normally be conducted at a temperature at least about 250° C. such as greater than about 300° C. or 375° C. and the maximum temperature in the reactor may be about 700° C. or 800° C. or perhaps higher such as 900° C.

The effluent from the dehydrogenation zone will contain the impure unsaturated organic products, various impurities including oxygenated hydrocarbons, noncondensable* gases and perhaps some unconverted feed, oxygen and steam. If air is used as the source of oxygen, nitrogen will be present in relatively large quantities as a noncondensable gas. Steam may be present in an amount up to 96 mol percent of the total effluent, such as from about 5 to 96 percent. On a water free basis the organic phase including dehydrogenated product, may unreacted feed, oxygenated hydrocarbons, polymer and tar and precursors thereof and any organic decomposition products usually range from about 1 to 50 mol percent of the effluent and generally will be within the range of or about 3 to 30 mol percent of the effluent. Also on a water free basis the noncondensable gases, such as nitrogen or $CO_2$, will usually be present in an amount of from or about 20 to 93 mol percent of the total effluent, but more often will be within the range of about 40 to 80 mol percent.

*The term "noncondensable" or "inert noncondensable" gases refers to those gases, other than hydrocarbons, such as nitrogen, $CO_2$ and CO, which do not condense under the conditions encountered.

The effluent gases leaving the dehydrogenation zone will generally be at a temperature of at least 400° C. or 450° C. with suitable ranges being between 450° C. or 500° C. and 800° or 900° C. depending upon the particular dehydrogenation process. According to the preferred embodiment of this invention the gases are fed directly into the catalyst bed for the destruction of oxygenated compounds or at least are fed to the catalyst bed prior to condensation of steam from the effluent gases. This catalyst bed may be incorporated into the same reactor chamber as the dehydrogenation bed, e.g., packing material may optionally be added between the dehydrogenation catalyst and the carbonyl destruction catalyst. Generally, the reactor effluent will not cool appreciably before the carbonyl destruction catalyst is encountered and, therefore, the temperature will be within the same ranges as for the reactor effluent. Optionally, prior to contacting with the carbonyl destruction catalyst the gaseous feed may be cooled or heated to give an optimum temperature for carbonyl destruction without adversely affecting the product. Also it is within the scope of the invention to remove portions or components of the reactor effluent prior to contacting with the catalyst. Normally the composition fed to the carbonyl destruction catalyst will contain at least 3 or 5 mols of uncondensed steam per mol of total organic compound such as hydrocarbon and may contain e.g. from 3 to 30 mols of steam. The reactor effluent will generally contain less than 5 mol percent free oxygen and may initially contain less than one mol percent of the reactor effluent. It is possible to add oxygen to the reactor effluent prior to contacting with the carbonyl destruction catalyst such as adding e.g. up to five mols of oxygen per mol of carbonyl compound but care should be exercised to avoid the explosive limits.

The presence of oxygen can be very detrimental in that the present decarbonylation catalyst tend to completely oxidize the unsaturated compound, e.g., hydrocarbon products. Hence, although oxygen can help keep the decarbonylation catalyst from coking, it may do so at the sacrifice of unsaturated product. For this reason the present invention is carried out with less than 5 mol percent and preferably less than 1 mole percent free oxygen present in the feed passing over the present catalyst.

The gaseous composition to be fed to the carbonyl destruction catalyst zone will preferably comprise, exclusive of any water present, about or from 3.5 to 80 mol percent of unsaturated hydrocarbon, about or from 0.005 to 2.5 mol percent of carbonyl compounds, and about or from 20 to 93 mol percent of noncondensable gases (i.e. noncondensable under the conditions of contact with the catalyst) all based on the total mols of gaseous composition being fed to the catalyst.

After the catalyst has been used for a period of time it may be regenerated such as by oxidation with air and/or with steam. Procedures for the regeneration of dehydrogenation catalysts to remove coke may be employed.

The following examples are only illustrative and are not intended to limit the invention. All percentages are by weight unless expressed otherwise.

EXAMPLES 1 – 5

A series of runs is made to illustrate the effect of certain catalysts on the destruction of carbonyl compounds in an effluent stream containing unsaturated hydrocarbons. In each instance 25 cc of catalyst of 6 to 8 mesh (U.S. Standard) is employed in a one inch Vycor reactor. The reactor temperature is controlled within the range of 555° to 575° C. The feed to the reactor is a mixture of 6 ml/min. of liquid carbonyl mixture of 0.3% by weight of 50% – 50% by weight mixture of formaldehyde and acetaldehyde which is vaporized by passing through a steam generator, 930 ml/min of gaseous nitrogen, and 575 ml/min of gaseous butadiene-1,3 with the gaseous volumes being calculated at 760 mm and 0° C. In the runs in which $CO_2$ is also added the carbonyl mixture is still fed at a rate of 6 ml per minute but the nitrogen is 720 ml/min, the butadiene-1,3 is 575 ml/min and the $CO_2$ is 210 ml/min. In all of these feeds steam is present in an amount of 13 mols per mol of hydrocarbon. The contact time of the feed with the catalyst is about 0.05 seconds. The percent removal of carbonyl compounds is analyzed by the hydroxylamine. HCl method, calculated on feed and effluent as $CH_3CHO$ (Reference Analytical Chem. Vol. 23, 1758). In the runs where a carrier is employed the percent carrier is the percent by weight based on the total weight of carrier and actives. The alumina carrier is an aluminum oxide carrier type AMC of 6 to 8 mesh (U.S. Standard). The ingredients in the catalyst are by weight percent. In some runs the catalyst is deliberately coated with coke to determine how well it performs under these adverse conditions which might be encountered on prolonged operation. The $CO_2$ is added in some runs to simulate the adverse condition of the feed. Sampling is started after 30 minutes in order to give to catalyst a chance to equilibrate. The product is then collected for a period of 80 minutes and the collected sample is analyzed for percent carbonyl removal.

| Ex. | Catalyst wt. % | Carrier, wt. % | $CO_2$ Present | % Carbonyl Removal |
|---|---|---|---|---|
| 1 | Quartz chips | — | No | 0 |
| 2 | SAS 350 $Al_2O_3$ | — | No | 0 |
| 3 | 50 $Sr(OH)_2$ | 50 alumina | No | 36[1] |
| 4 | Calcium aluminate | — | " | 75[2] |
| 5 | 35 $Ca_3(PO_4)_2$ | 65 alumina | " | 0 (catalyst coked) |

[1] Repeat with $CO_2$ gave 4%
[2] Calcium aluminate in all of the examples is Alcoa CA 25 having the empirical molar formula CaO . 2.5 $Al_2O_3$.

EXAMPLES 6-10

A series of runs is made feeding a varporized mixture of 6 liquid ml per minute of 0.3% by weight mixture of 50% formaldehyde and 50% acetaldehyde and 1500 cc gaseous nitrogen per minute through a 25 cc catalyst bed of 6 to 8 mesh size. Runs are made from 4.2 to 8.2 minutes. The reactor is Vycor and the catalyst temperature is 540 to 575° C. Percentages are by weight.

| Example | Catalyst wt. % | Carrier wt. % | % Carbonyl Removal |
|---|---|---|---|
| 6 | Quartz chips | — | <1 |
| 7 | CaO | — | 85 |
| 8 | $CaCO_3$ | — | 50 |
| 9 | $TiO_2$ | — | 58 |
| 10 | 50 $Ca_2SiO_4$ 50 calcium aluminate | — | 91 |

A run is made to determine the effect of the catalyst of this invention on unsaturated hydrocarbon products being fed to the catalyst for carbonyl removal. In order to be efficient the catalyst should not only be efficient in removing carbonyls but should not be destructive of the unsaturated products being fed to the carbonyl removal catalyst. For example, in the case of the oxidative dehydrogenation of butylenes to butadiene the effluent contains butadiene contaminated with carbonyl compounds and the effluent from this reaction can be fed to the catalyst for the removal of carbonyl compounds. The catalyst for the removal of the carbonyl compounds should selectively destroy carbonyl compounds but preferably does not destroy butadiene.

EXAMPLES 11 – 23

A series of runs is made feeding a mixture of:

| | ml/min |
|---|---|
| Aldehyde solution (50/50 mixture of HCHO and $CH_3CHO$) | 6 |
| nitrogen | 720 |
| butadiene-1,3 | 575 |
| $CO_2$ | 210 |

25 cc. of 6 – 8 mesh of the respective catalyst are employed. Examples 11, 12, 13 and 21 – 23 are the results of a sample taken for 40 minutes and the remaining examples are the results of an 80 minute sample and in all examples the catalyst is first run for 30 minutes for equilibration.

| Ex. | Catalyst Composition wt. % | Carrier wt. % | % Carbonyl Removal |
|---|---|---|---|
| 11 | ZnO (Harshaw Zn 0401) | | 49 |
| 12 | $Bi_2O_3 + Fe_2O_3$ (1:1 mol ratio, mixed) | | 84 |
| 13 | 30 $Fe_2O_3$[1] | 70 alumina[2] | 46 |
| 14 | 95 $WO_3$ (Harshaw W-602T) | | 10 |
| 15 | 30 $CeO_2$[1] | 70 alumina | 45 |
| 16 | 33 ZnS[1] | 67 alumina | 79 |
| 17 | ZnS[1] | | 73 |
| 18 | CoO | Girdler F301 | 64 |
| 19 | 33 $BiFeO_3$ | 67 alumina | 26 |
| 20 | 50 $ZrO_2$ | 50 alumina | 73 |

[1] Catalyst is prereduced with a mixture of steam and hydrogen for 3 hours at 560° C.
[2] Alumina used in the series of runs is 6-8 mesh (U.S. Standard) Type AMC.

| Ex. | Catalyst Composition, Wt. % | % Aldehyde Removal (successive runs) | Remarks[2] |
|---|---|---|---|
| 21 | AMC | <4 | Considerable |
| 22 | CoO/suport (Girdler T-301) | 64, 63 | acetone, little |
| 23 | 30% $Fe_3O_4$/AMC | 76, 77[1] | acetaldehyde |

[1] First run over unreduced $Fe_3O_4$, second run after a reduction cycle.
[2] Qualitative characterization of residual carbonyls, acetone is produced during the carbonyl destruction.

We claim:

1. In a vapor phase process for the preparation of unsaturated hydrocarbons comprising
    catalytic oxidative dehydrogenation of a feed stream of hydrocarbon compounds having 4 to 8 carbon atoms to produce an unsaturated hydrocarbon product stream having a greater degree of ethylenic unsaturation than said feed stream and containing organic carbonyl compounds as an impurity wherein the improvement comprises contacting only said product stream in vapor phase at a temperature in the range of 250° to 800° C and containing less than 5 mol percent free oxygen with a solid catalyst for destroying said carbonyl compounds and consisting essentially of ZnS.

* * * * *